(12) United States Patent
Krimsky

(10) Patent No.: US 10,799,092 B2
(45) Date of Patent: Oct. 13, 2020

(54) SYSTEM AND METHOD FOR CLEANSING SEGMENTS OF A LUMINAL NETWORK

(71) Applicant: COVIDIEN LP, Mansfield, MA (US)

(72) Inventor: William S. Krimsky, Forest Hill, MD (US)

(73) Assignee: COVIDIEN LP, Mansfield, MA (US)

(*) Notice: Subject to any disclaimer, the term of this patent is extended or adjusted under 35 U.S.C. 154(b) by 357 days.

(21) Appl. No.: 15/700,243

(22) Filed: Sep. 11, 2017

(65) Prior Publication Data

US 2018/0078119 A1 Mar. 22, 2018

Related U.S. Application Data

(60) Provisional application No. 62/396,322, filed on Sep. 19, 2016.

(51) Int. Cl.
*A61B 1/00* (2006.01)
*A61B 5/06* (2006.01)
(Continued)

(52) U.S. Cl.
CPC ...... *A61B 1/00082* (2013.01); *A61B 1/00085* (2013.01); *A61B 1/015* (2013.01); *A61B 1/018* (2013.01); *A61B 5/062* (2013.01); *A61B 10/0045* (2013.01); *A61B 10/02* (2013.01); *A61M 13/00* (2013.01); *A61M 16/0404* (2014.02); *A61M 16/0459* (2014.02); *A61M 16/0479* (2014.02); *A61M 25/007* (2013.01);
(Continued)

(58) Field of Classification Search
CPC ..... A61B 1/00082; A61B 1/018; A61B 34/20; A61B 5/062; A61B 6/486; A61B 10/0045; A61B 10/02; A61B 18/00; A61B 1/00085; A61B 1/015; A61B 1/2676; A61B 2017/00809; A61B 2034/105; A61B 2034/2051; A61B 2034/2072; A61B 2090/3925; A61M 13/00; A61M 16/0404; A61M 16/0459; A61M 16/0479; A61M 2025/1052; A61M 25/007; A61M 25/1011; A61K 9/0073
See application file for complete search history.

(56) References Cited

U.S. PATENT DOCUMENTS 5,029,580 A 7/1991 Radford et al.
5,165,420 A 11/1992 Strickland
(Continued)

FOREIGN PATENT DOCUMENTS

EP 2508221 A1 10/2012

OTHER PUBLICATIONS

Extended European Search Report for application No. 171919327 dated Feb. 26, 2018, 9 pages.
(Continued)

*Primary Examiner* — Brandy S Lee

(57) ABSTRACT

A method and system for instilling a medium into portions of a luminal network is provided. The method includes generating a model of a luminal network based on images of the luminal network, determining a location of a treatment target in the luminal network, navigating a bronchoscope through the bronchial tree to a target, guiding a catheter through the bronchoscope, dispensing medium to the target from a distal end of the catheter, and removing a quantity of medium from the luminal network.

20 Claims, 7 Drawing Sheets

(51) Int. Cl.

| | |
|---|---|
| *A61B 1/018* | (2006.01) |
| *A61M 25/00* | (2006.01) |
| *A61M 16/04* | (2006.01) |
| *A61M 13/00* | (2006.01) |
| *A61M 25/10* | (2013.01) |
| *A61B 1/015* | (2006.01) |
| *A61B 10/00* | (2006.01) |
| *A61B 10/02* | (2006.01) |
| *A61B 6/00* | (2006.01) |
| *A61K 9/00* | (2006.01) |
| *A61B 34/20* | (2016.01) |
| *A61B 34/10* | (2016.01) |
| *A61B 90/00* | (2016.01) |
| *A61B 17/00* | (2006.01) |

(52) U.S. Cl.
CPC .......... *A61M 25/1011* (2013.01); *A61B 6/486* (2013.01); *A61B 34/20* (2016.02); *A61B 2017/00809* (2013.01); *A61B 2034/105* (2016.02); *A61B 2034/2051* (2016.02); *A61B 2034/2072* (2016.02); *A61B 2090/3925* (2016.02); *A61K 9/0073* (2013.01); *A61M 2025/1052* (2013.01)

(56) References Cited

U.S. PATENT DOCUMENTS

| | | | |
|---|---|---|---|
| 5,246,012 | A | 9/1993 | Strickland |
| 6,398,775 | B1 | 6/2002 | Perkins et al. |
| 2003/0051733 | A1* | 3/2003 | Kotmel .................. A61B 5/055 128/207.14 |
| 2006/0095066 | A1 | 5/2006 | Chang et al. |
| 2006/0184016 | A1* | 8/2006 | Glossop ............... A61B 1/2676 600/434 |
| 2008/0114286 | A1 | 5/2008 | Hamel et al. |
| 2010/0041949 | A1 | 2/2010 | Tolkowsky |
| 2011/0245665 | A1 | 10/2011 | Nentwick |
| 2012/0046521 | A1* | 2/2012 | Hunter .................. A61B 5/415 600/104 |
| 2014/0018732 | A1 | 1/2014 | Bagaoisan et al. |
| 2014/0142376 | A1* | 5/2014 | Ghosh ................... A61B 1/018 600/104 |
| 2015/0272666 | A1 | 10/2015 | Wang |

OTHER PUBLICATIONS

Australian Examination Report for application No. 2017232030 dated Mar. 9, 2018, 9 pages.
Australian Office Action issued in Application No. 2017232030, dated Aug. 1, 2018.
Canadian Office Action issued in Application No. 2979117, dated Aug. 2, 2018.

* cited by examiner

SYSTEM AND METHOD FOR CLEANSING SEGMENTS OF A LUMINAL NETWORK

CROSS REFERENCE TO RELATED APPLICATION

The present application claims the benefit of and priority to U.S. Provisional Application Ser. No. 62/396,322, filed on Sep. 19, 2016 the entire contents of which are incorporated herein by reference.

BACKGROUND

1. Technical Field

The present disclosure relates to surgical instruments and, more specifically, to catheters and methods of use for dispensing a medium to a portion of a luminal network within a body.

2. Discussion of Related Art

Bronchiectasis is a condition characterized by significant and irreversible dilatation or enlargement of the bronchi resulting from changes in the elastic and muscular components of the bronchial wall. Initial lung damage often begins in childhood and stems from infections such as whooping cough and measles. The airway dilatation results in progressive difficulties with mucus and secretion clearance. Shortness of breath and increasing fatigue follow as lung function decreases. In an advanced condition, bronchiectasis can lead to respiratory failure and heart failure.

Bronchiectasis also causes patients to become more susceptible to virulent strains of bacteria colonizing the tracheobronchial tree. Bacterial organisms enter the distal airway by inhalation, aspiration or by hematogenous seeding and colonize the site of the damaged tissue. Antibiotics are effective initially against such bacterial infections once they have developed. However, antibiotic treatments often require repeated hospitalization. As the infections progress, prolonged courses of intravenous antibiotics are required resulting in high cost and significant consumption of healthcare resources. Intravenous antibiotics may also cause unwanted side effects, may include issues with vascular access, and because it is particularly difficult to clear the lungs of bacteria in their entirety, may be associated with the development of antibiotic resistant bacteria. Once substantive antimicrobial resistance develops, the process accelerates further resulting in even longer, more complex hospitalizations as both the amount and types of antibiotics are used in an effort to stem the illness. Yet, despite the intensity of the interventions, these approaches may be ineffective at controlling the disease at this point In the case of external infections, treatments include cleansing the infected area with an antibiotic-containing lavage solution and applying clean dressings. Solution cleansing provides a faster and more complete elimination of bacterial infections. In rare circumstances, such as the treatment of pulmonary alveolar proteinosis, a saline lavage is used to displace exuberant proteins that fill the alveolar spaces to treat lung infections. The procedure is known as a whole lung lavage. A similar procedure is used for rinsing of the sinuses and the nasal passages and has resulted in well documented improvements. In a whole lung lavage procedure, a patient is put under general anesthesia and one lung at a time undergoes a procedure of filling the lung with a medium, typically saline, and then letting it drain with the use of significant chest PT to enhance drainage. During the procedure, the patient is put at significant risk as the lung not being treated is relied upon to ventilate the patient, which is already compromised by the same process that required the lavage in the first place and any spillover into the lung providing ventilation could cause a critical situation, severely inhibiting gas exchange and oxygenation. Even when successful, the procedure can only be performed at medical centers possessing high levels of experience with the procedure and the procedure is lengthy and extensive.

Despite the issues with whole lung lavage, lavage washing and rinsing remains a viable concept and an effective treatment if it can be performed safely and more cost effectively. Therefore, there is a need for an apparatus that facilitates controlled delivery of fluids and other mediums to target locations at or beyond the distal tip of the bronchoscope.

SUMMARY

Provided in accordance with the present disclosure is a method of instilling a medium into portions of a luminal network. The method includes generating a model of a luminal network based on images of the luminal network, determining a location of a treatment target in the luminal network, navigating a bronchoscope through the bronchial tree to a target area, guiding a catheter through the bronchoscope, dispensing medium to the target area from a distal end of the catheter, and removing a volume of the medium from the luminal network.

In an aspect of the present disclosure, the method further includes tracking a location of a location sensor coupled to the bronchoscope while the location sensor is navigated within the luminal network and displaying guidance for navigating the location sensor within the luminal network.

In another aspect of the present disclosure, the method further includes generating an electromagnetic field about the luminal network and inserting the location sensor into the electromagnetic field. The location sensor includes magnetic field sensors configured to sense the magnetic field and to generate position signals in response to the sensed magnetic field.

In an aspect of the present disclosure, the method further includes measuring the volume of medium removed from the luminal network and determining whether the volume of the medium removed from the luminal network equals or exceeds a threshold volume based on a volume of the dispensed medium.

In another aspect of the present disclosure, the method further includes inflating a first balloon coupled to the distal end of the catheter until the first balloon contacts walls of the luminal network creating a seal. The first balloon, when inflated, prevents the medium from advancing past the balloon such that the medium remains distal to the first balloon.

In an aspect of the present disclosure, the method further includes inflating a second balloon coupled to the distal end of the catheter, distal to the first balloon, until the second balloon contacts the walls of the luminal network creating a seal. The second balloon, when inflated, prevents the medium from advancing such that the medium remains proximal to the second balloon. The first balloon and the second balloon isolate a volume of the lungs.

In an aspect of the present disclosure, the medium is at least one of an antibacterial, an antifungal, an antiviral, and an immunotherapy solution.

In another aspect of the present disclosure, the medium is at least one of a fluid, an aerosol, a powder, an epoxy, and a sealant.

In yet another aspect of the present disclosure, if atelectasis is induced, the dispensing of the medium causes the portion of the lung to inflate.

In an aspect of the present disclosure, the method further includes sensing that the targeted portion of the lung has atelectasized.

In another aspect of the present disclosure, the medium is dispensed and removed using passive dispensing techniques.

In another aspect of the present disclosure, the medium is dispensed and removed using a manual syringe.

In yet another aspect of the present disclosure, the medium is dispensed using a pump.

In another aspect of the present disclosure, the method further includes measuring an internal luminal pressure and halting medium dispensing if the internal luminal pressure exceeds a pressure value.

Provided in accordance with the present disclosure is a system for instilling medium into an isolated portion of a luminal network. In an aspect of the present disclosure, the system includes an extended working channel navigable to a treatment target within a patient and a catheter, extendible through the extended working channel and configured to transport medium to the treatment target. The catheter includes a distal and a proximal end, an isolation mechanism configured to contact walls of the luminal network in order to prevent the medium and air from passing, thereby isolating a portion of the lungs, an inlet at the proximal end configure to receive liquid, and one or more outlets near the distal end configured to dispense the liquid to the treatment target.

In another aspect of the present disclosure, the isolation mechanism includes one or more inflatable balloons near the distal end of the catheter configure to inflate and contact with the walls of the luminal network in order to create a barrier.

In another aspect of the present disclosure, the isolation mechanism includes a tapered distal portion of the catheter which is configured to be wedge between the walls of the luminal network In another aspect of the present disclosure, the isolation mechanism includes one or more endobronchial valves.

In another aspect of the present disclosure, the system further includes a location sensor coupled to the extended working channel, an electromagnetic field generator configured to detect the location of the location sensor as it is navigated within the luminal network, a display capable of displaying an image of the location sensor within the body, and a computing device including a processor and a memory storing instructions. The instructions, when executed by the processor, cause the computing device to generate a model of the luminal network based on images of the luminal network, identify the treatment target within the model of the luminal network, and track the location of the location sensor while the location sensor is navigated within the luminal network.

In a further aspect of the present disclosure, the system further includes a medium meter configured to measure a volume of the medium as it passes the inlet.

In another aspect of the present disclosure, the one or more balloons create a segment to be filled with medium.

In a further aspect of the present disclosure, the catheter further includes an air channel extending beyond each of the one or more balloons, allowing air to bypass the segment to be filled with medium.

In another aspect of the present disclosure, the medium is at least one of an antibacterial, an antifungal, an antiviral, and an immunotherapy solution.

In a further aspect of the present disclosure, the medium is at least one of a fluid, an aerosol, a powder, an epoxy, and a sealant.

In another aspect of the present disclosure, the system further includes a pressure sensor configured to determine if a portion of the luminal network has collapsed or if an internal pressure of the portion of the luminal has exceeded a pressure threshold.

In a yet another aspect of the present disclosure, the system further includes a bag coupled to the catheter and configured to hold the medium and a valve configured to be toggled to between an open and a closed position to allow flow of the medium to and from the bag.

In a further aspect of the present disclosure, the system further includes a syringe configured to push the liquid through the inlet and out the outlet and to the treatment target and to withdraw the medium from the treatment target.

In another aspect of the present disclosure, the system further includes a pump configured to push the medium through the inlet and out the outlet to the treatment target and to withdraw the medium from the treatment target.

Further, to the extent consistent, any of the aspects described herein may be used in conjunction with any or all of the other aspects described herein.

BRIEF DESCRIPTION OF THE DRAWINGS

Various aspects and features of the present disclosure are described hereinbelow with references to the drawings, wherein.

DETAILED DESCRIPTION

Figure 1:
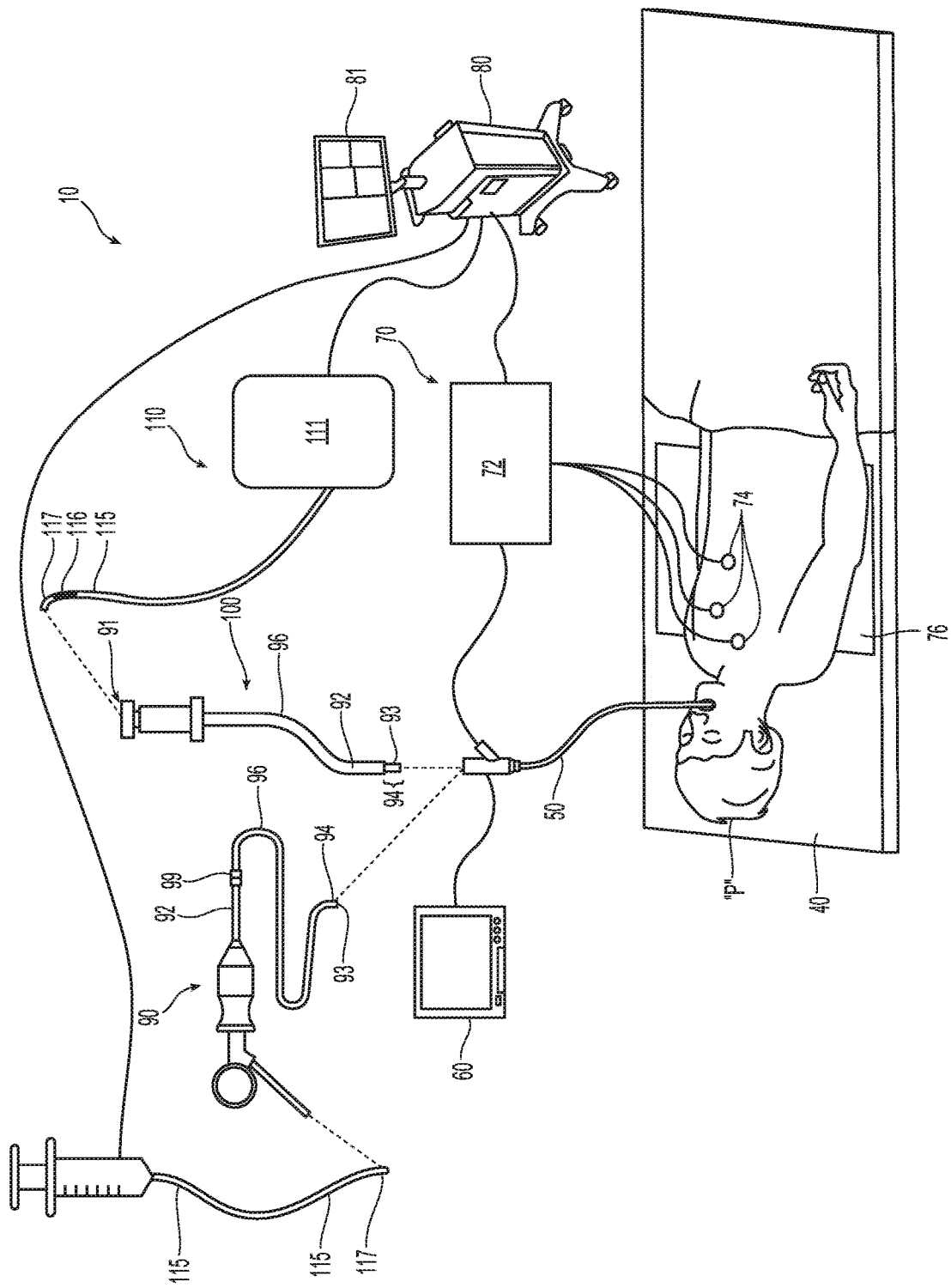
FIG. 1 is a perspective view of a system provided in accordance with the present disclosure configured for navigating a catheter to an area of interest and applying medium.

The present disclosure is directed, in part, to methods and systems for the treatment of bronchiectasis using lobar or segmental isolation lavage techniques. The lobar or segmental isolation lavage methods of the present disclosure involve navigating to a target region requiring treatment. Such a localized approach allows for controlled dispensing without the risks associated with a whole lung lavage procedure.

Treatment includes instillation of a medium, such as a cleansing fluid, an antibacterial medium, an antifungal medium, an antiviral medium, and an immunotherapy solution, or a medium comprising beneficial microbes. The medium may be, for example, a saline solution, hyperoxygenated solutions, and antibiotic-containing solutions, containing antibiotics such as β-lactam antibiotics. The medium may include specifically known beneficial microbes, or alternatively, the medium may include a phlegm sample taken from a healthy host in order to achieve introduction of all beneficial microbes present in the healthy host.

The disclosure is further directed to localized dispensing and removing medium one or more times to the target region, killing and/or washing away harmful microbiomes. If a medium comprising beneficial microbes is applied, the medium may be dispensed in a gentler manner to allow the microbes to take hold in the effected regions.

The disclosure is further directed to instillation of various types of solid, liquid, gaseous, and other types of media. Particularly, treatment instillation may be performed with a fluid, an aerosol, a powder, an epoxy, and a sealant. Fluids, aerosols, and powders may be used in applying any of the above described cleansing fluids, antibacterial mediums, antifungal mediums, antiviral medium, and an immunotherapy solution an antimicrobial fluid, or a fluid medium comprising beneficial microbes. The medium structure merely depends upon with ailment and the treatment protocol. For instance, a fluid may be used preferable for a cleansing procedure or any other procedure where an entire volume of the lungs is to be filled. A powder or other solid material may be preferable so that a coating may be applied to the lungs without filling the lungs. Furthermore, any of the potential mediums may be heated or cooled to a temperature that may allow therapeutic application. For example, cooled mediums may be used to decrease inflammation that may result from application of the medium and tissue reactions resulting therefrom or to avoid overheating resulting from chemical reactions between the medium and elements in the lungs. As an additional example, applying a heated or cooled medium may enable the medium to kill additional microbes through conductive heat transfer. Heated and cooled mediums may be applied individually, together, or separately in a sequential order that may be repeated through a number of cycles to ensure the lungs are cleared of unwanted microbes.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

With reference to FIG. 1, an electromagnetic navigation (EMN) system 10 is provided in accordance with the present disclosure. Among other tasks that may be performed using the EMN system 10 are planning a pathway to target tissue, navigating a catheter assembly to the target tissue, navigating a biopsy tool or treatment tool, such as an ablation catheter, to the target tissue to obtain a tissue sample from the target tissue using the biopsy tool, digitally marking the location where the tissue sample was obtained, and placing one or more echogenic markers at or around the target.

EMN system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a workstation 80 including software and/or hardware used to facilitate pathway planning, identification of target tissue, navigation to target tissue, and digitally marking the target tissue.

FIG. 1 also depicts two types of catheter guide assemblies 90, 100. Both catheter guide assemblies 90, 100 are usable with system 10 and share a number of common components. Each catheter guide assembly 90, 100 includes a handle 91, which is connected to a navigation catheter, such as extended working channel (EWC) 96. EWC 96 is sized for placement into the working channel of a bronchoscope 50. In operation, a locatable guide (LG) 92, including an electromagnetic (EM) sensor 94, is inserted into EWC 96 and locked into position such that EM sensor 94 extends a desired distance beyond a distal tip 93 of EWC 96. The location of EM sensor 94, and thus the distal end of EWC 96, within an electromagnetic field generated by electromagnetic field generator 76 can be derived by tracking module 72, and computing device 80. Catheter guide assemblies 90, 100 have different operating mechanisms, but each contain a handle 91 that can be manipulated by rotation and compression to steer distal tip 93 of LG 92 and EWC 96. An example of catheter guide assemblies 90 are those currently marketed and sold by Medtronic PLC under the name SUPERDIMENSION® Procedure Kits. Similarly, an example of catheter guide assemblies 100 are currently sold by Medtronic PLC under the name EDGE™ Procedure Kits. Both kits include a handle 91, EWC 96, and LG 92. For a more detailed description of the catheter guide assemblies 90, 100, reference is made to commonly-owned U.S. Pat. No. 9,247,992 entitled MICROWAVE ABLATION CATHETER AND METHOD OF UTILIZING THE SAME, filed on Mar. 15, 2013, by Ladtkow et al., the entire contents of which are incorporated herein by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in U.S. Pat. No. 6,188,355, entitled WIRELESS SIX-DEGREE-OF-FREEDOM LOCATOR, filed on Dec. 14, 1998, by Gilboa, and published PCT Application Nos. WO 00/10456 and WO 01/67035, the entire contents of each of which are incorporated herein by reference, or any other suitable positioning measuring system, is utilized for performing navigation, although other configurations are also contemplated. Tracking system 70 is configured for use with catheter guide assemblies 90, 100 to track the position of EM sensor 94 as it moves in conjunction with EWC 96 through the airways of the patient, as detailed below.

As shown in FIG. 1, EM field generator 76 is positioned beneath the patient. EM field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to computing device 80, which includes an application 81 which uses data collected by sensors 74 to calculate a patient coordinate frame of reference.

Although EM sensor 94 is described above as being included in LG 92 it is also envisioned that EM sensor 94 may be embedded or incorporated within catheter 105 where catheter 105 may alternatively be utilized for navigation without need of LG 92 or the necessary tool exchanges that use of LG 92 requires.

During navigation, EM sensor 94, in conjunction with tracking system 70, enables tracking of EM sensor 94, and thereby LG 92 or a treatment tool, such as catheter 105, is advanced through the patient's airways. As LG 92 or catheter 115 is navigated to a target location within the patient, the sensed location of EM sensor 94 is displayed on the computing device 80 enabling the clinician to follow the pathway that was developed during the planning phase and reach a desired target area for treatment. Following arrival at the target area, the LG 92 may be removed allowing the insertion of catheter 115. Alternatively, catheter 115 need not be inserted after LG 92 is removed. Rather, EWC 96 may function as the medium conduit. Moreover, catheter 115 may be excluded altogether from the system and any function described herein as being performed by catheter 115 may be performed by EWC 96. Additionally, any features described as being part of catheter 115 in the present application may also be features included as part of EWC 96.

Also shown in FIG. 1 are medium dispensing devices 110. Medium dispensing devices 110 include catheter 115 and medium control devices 111, 113. Medium control devices 111, 113 contain a medium reservoir (not shown). Medium control devices 111, 113 generate pressure forcing medium from the medium reservoir through catheter 115 to be dispensed to and removed from treatment target T. Alternatively, a reservoir filled with the medium may be placed above a patient allowing the medium to flow passively into the lungs. The reservoir may be a bag with a petcock valve at its opening or on the catheter. The valve may be switch between an open and closed position. When the valve is open, gravity moves the medium through the catheter to the treatment target. When the procedure is complete and the medium is ready to be removed, the bag may similarly be placed below the patient to allow the medium to flow out After some or all of the medium is dispensed to treatment target T, medium control devices 111, 113 generate vacuum force drawing the medium away from the treatment target, through catheters 115, and the medium flows back into the original medium reservoir or into a chamber for discarded medium. Manual medium control device 113 includes a plunger 119 or alternatively, a bulb and air valve combination configured to push the recovered medium so that it is discharged out of an opening in distal end 117 of catheter 115. By retracting plunger 119, a vacuum is generated and medium is withdrawn. For passive removal of the medium, the same reservoir or another container may be placed below the patient to allow the medium to flow out of the lungs and into the reservoir or container. The recovered medium may then be discarded or tested for microbes, concentrations of different substances, etc.

Automatic medium control device 111 may include any device capable of generating pressure and/or a vacuum force including, but not limited to, a positive displacement pump, such as a screw pump or a peristaltic pump, an impulse pump, a valueless pump, etc. Automatic medium control device 111 connects to and communicates with workstation 80 or another computing device. Workstation 80 generally controls automatic medium control device 111, determining medium dispensing parameters and receiving data from sensors within automatic medium control device 111 to be displayed or used to adjust medium dispensing parameters. However, automatic medium control device 111 may independently include hardware, similar to the hardware of workstation 80 shown in FIG. 7, and software to independently control medium dispensing, process data, and/or display medium control data.

Catheters 105 are sized for and insertable into catheter guide assemblies 90, 100 following navigation to a target and removal of LG 92. Catheters 105 provide a track for medium from medium control devices 111, 113 to a treatment target T. Catheter 105 may additionally allow gases, such as air, or additional mediums to pass or be pumped to and from treatment target T. Additional space within catheter 105 may be provided for wiring connecting sensors (similar to those of the LG) located at distal end 117 of catheter 115. Catheter 105 may include medium flow sensor 116 configured to determine how much medium passes through, the direction of the medium, and the rate at which the medium is flowing. Medium flow sensor 116 provides measured flow information to workstation 80 to be displayed and can indicate that the equipment has malfunctioned or there is a concern with the patient. Medium flow sensor 116 may be, for example, a differential pressure flow meter, an orifice plate, a venturi tube, a flow nozzle, a sonic nozzle, a variable area flow meter, a velocity flow meter, a calorimetric flow meter, a turbine flow meter, a vortex flow meter, etc., or any combination thereof. Medium flow sensor 116 is depicted near the distal end of catheter 105, but may be found anywhere along catheter 105 or within medium control devices 111, 113.

Catheter 105 is further configured for use in conjunction with tracking system 70 to facilitate navigation of catheter 105 to treatment target T, tracking of a location of catheter 105 as they are manipulated relative to the target tissue to obtain the tissue sample, and/or marking the location where the tissue sample was obtained.

Although navigation is detailed above with respect to EM sensor 94 being included in LG 92 it is also envisioned that EM sensor 94 may be embedded or incorporated within catheter 105 where catheter 105 may alternatively be utilized for navigation without need of LG 92 or the necessary tool exchanges that use of LG 92 requires. A variety of tools are described in Pub. Nos. US 2015/0141869 and US 2015/0265257 both entitled DEVICES, SYSTEMS, AND METHODS FOR NAVIGATING A BIOPSY TOOL TO A TARGET LOCATION AND OBTAINING A TISSUE SAMPLE USING THE SAME, filed May 21, 2015 and Sep. 24, 2015, respectively, by Costello et al., and in Pub. No. WO2015076936 having the same title and filed Sep. 30, 2014, by Costello et al., the entire contents of each of which is incorporated herein by reference and useable with EMN system 10 as described herein. Catheter 105 may be navigated in the same manner as a biopsy tool described in these references.

During procedure planning, workstation 80 utilizes computed tomographic (CT) image data for generating and viewing the 3D model of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous procedures were performed, including the dates, times, and other identifying information regarding the procedure. These marks may also be selected as the target to which a pathway can be planned. Once selected, the pathway is saved for use during the navigation procedure. An example of a suitable pathway planning system and method is described in Pub. Nos. US 2014/0281961; US 2014/0270441; and 2014/0282216, all entitled PATHWAY PLANNING SYSTEM AND METHOD, filed on Mar. 15, 2014, by Baker, the entire contents of each of which is incorporated herein by reference. During navigation, EM sensor 94, in conjunction with tracking system 70, enables tracking of EM sensor 94 and/or catheter 105 is advanced through the patient's airways.

Workstation 80 may also utilize computed tomographic (CT) image data to determine a volume of various regions of the lungs. The volume determination may be used to determine a volume of air that must be removed from the lungs before applying a medium. Additionally, the volume determination may be used to determine a volume of the medium applied to the lungs.

Figure 2:
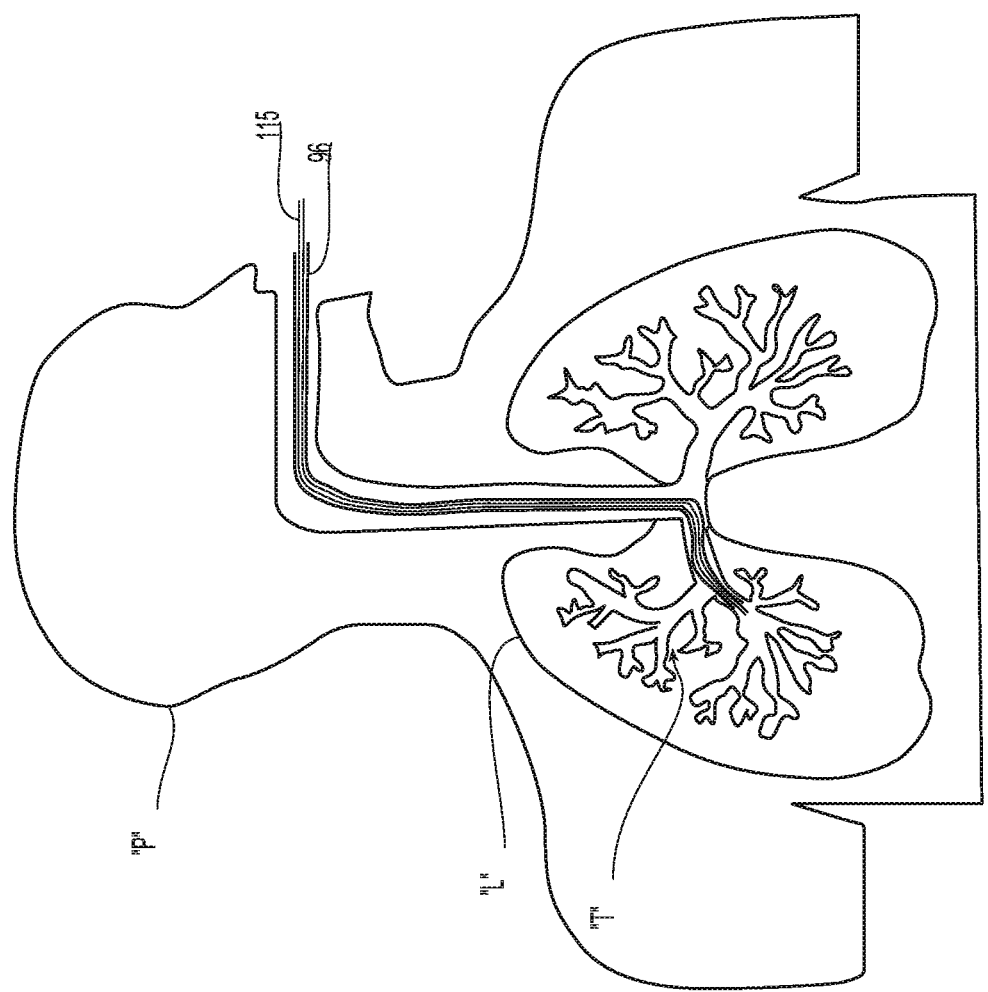
FIG. 2 is a schematic, plan view of the extended working channel shown in FIG. 1 positioned within a bronchus of the patient with the catheter extending distally therefrom.

Turning now to FIG. 2 is a schematic, plan view of EWC 96 within the trachea of the patient with catheter 115 within EWC 96 and extending into a branch of the bronchial tree. Medium flows through catheter 115 into the lungs L. Once the medium reaches distal end 115 of catheter 115, the medium is expelled through one or more openings. The medium flows into branches of the bronchial tree containing one or more treatment targets T, filling them. Once the medium has filled the branches of the bronchial tree containing one or more treatment target areas T, an exposure of one or more treatment targets T to the medium can assured. The medium remains in the lungs for a period of time to allow the medium to saturate the area, rinse the area, and/or kill bacterial from treatment targets T.

After the appropriate time has passed, medium control devices 111, 113 generate a vacuum force to withdraw the medium from the branches of the bronchial tree, through the same openings at distal end 117 of catheter 115. Alternatively, the medium may be removed using a passive lung drainage device and a passive lung drainage technique. Drainage devices that may be used include, for example, chest drains, thoracic catheters, thoracostomy tubes, trocar tubes, and intercostal drains, all commonly known as chest tubes. Catheter 115 may, in and of itself, be used as a chest tube. Once the medium application is complete, the proximal end of catheter 115 may be removed from medium dispensing device 110 and positioned below the patient, allowing the medium to flow through catheter 115. The medium flows freely once a negative pressure at the proximal end of catheter 115 is established. Moreover, catheter 115 may also be connected to a bottle chest drain system (including one or more bottles for collection, water sealing, and suction control), a chambered disposable chest drain system, an infant chest drainage system, or a closed wound reservoir system as needed. Once the medium has been removed and prior to removal of catheter 115 and EWC 96, air may be pumped or otherwise introduced through the catheter into the bronchial tree to reinflate the lung if it has collapsed.

Figure 3:
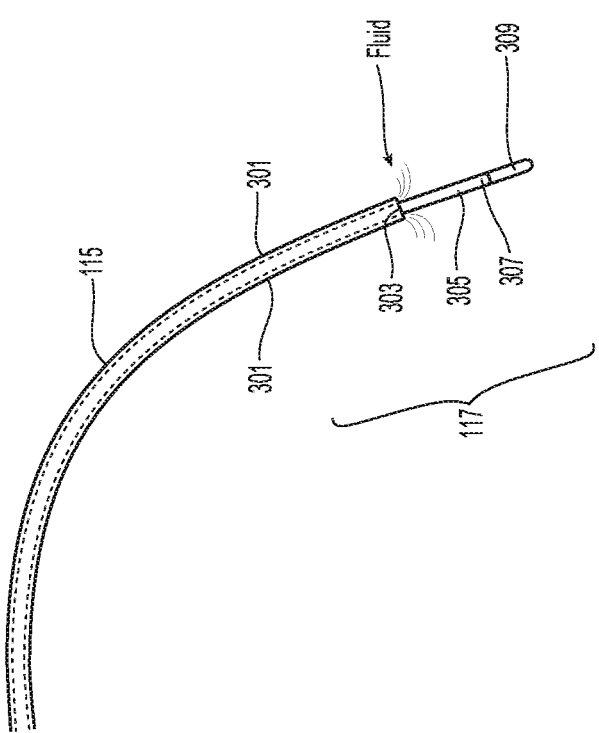
FIG. 3 is a perspective view of an illustrative embodiment of a distal end of a catheter in accordance with the present disclosure.
Figure 4:
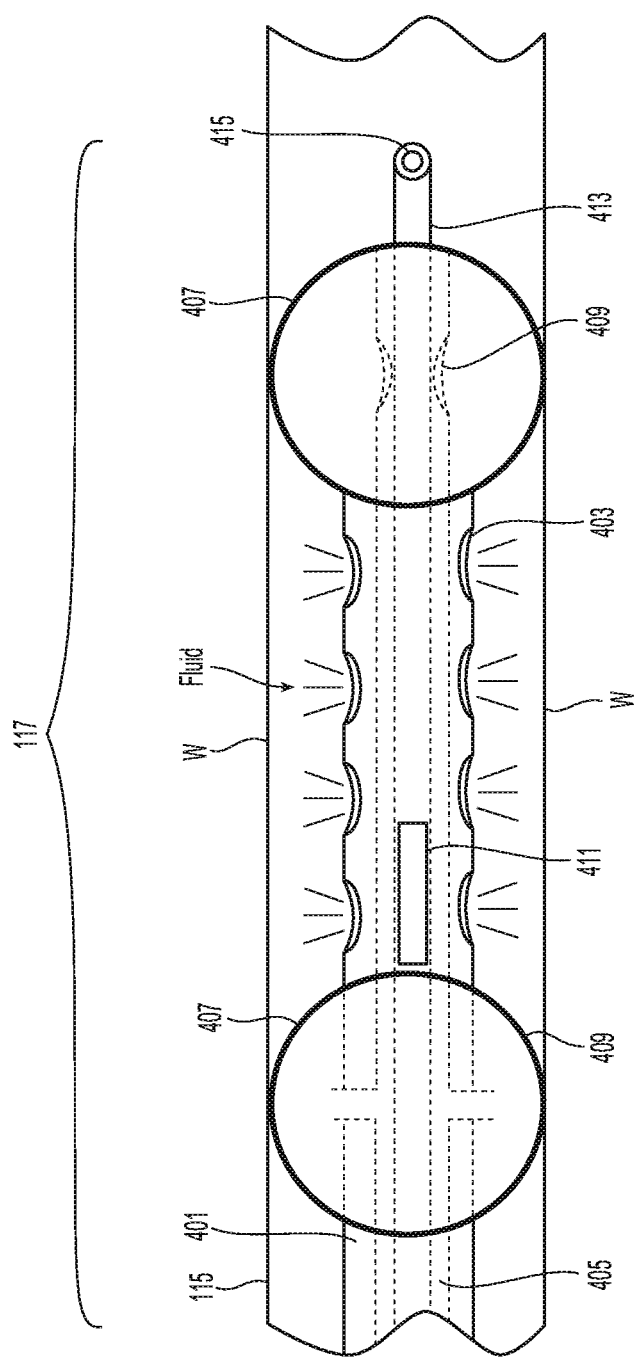
FIG. 4 is a diagram view of another illustrative embodiment of a distal end of a catheter in accordance with the present disclosure.
Figure 5:
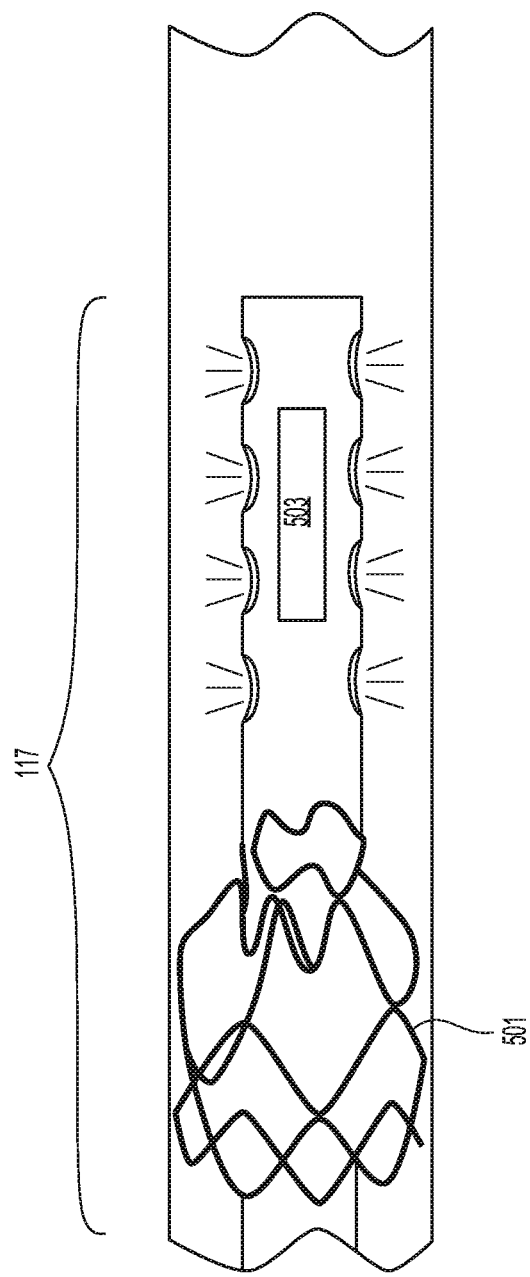
FIG. 5 is a diagram view of yet another illustrative embodiment of a distal end of a catheter in accordance with the present disclosure.

FIGS. 3-5 show exemplary embodiments of distal end 117 of catheter 115 used to expel the medium into the lungs. In FIG. 3, distal end 117 of catheter 115 includes one or more medium channels 301, medium outlet 303, and auxiliary shaft 305. Medium channels 301 run the length of catheter 115 and allow the medium to travel from medium control device 111, 113. Pressure generated at medium control device 111, 113 forces the medium through medium channels 301 and out outlet 303. The medium flows from outlet 303 into the bronchial tree, influenced only by the direction and force at which the medium is expelled from outlet 303 and gravity. Additionally, the system can be configured such that medium instillation is automatically slowed or stopped when a given pressure or volume is reached. The pressure or volume can be estimated in a number of different ways (CT scanning, etc.) and can also be interpreted to mean that the target zone in question has been fully saturated with the medium or aerosol, etc. Those having ordinary skill in the art will understand that reaching a given pressure or volume in the target area may infer further meanings commonly known in the art. After the medium has been dispensed to the treatment target and an appropriate amount of time has passed, potentially determined by a timer instantiated by program 81 or by the disease process being targeted, medium control device 111, 113 generates a vacuum force to withdraw the medium from the target locations through outlet 303, or, in the alternative through auxiliary opening 307 of auxiliary shaft 305.

Catheter 115 of FIG. 3 can effectively provide the medium to limited, precise targets where, for example, merely a coating of the medium is necessary, and where there is less potential for dangerous runoff of the medium. Dispensing of the medium to a target positioned physically below a treatment target is particular effective. In order to reduce the potential for runoff using the exemplary embodiment of FIG. 3, an aerosol medium may be used. The aerosol exits medium outlet 303, expands to fills a local volume of the lungs, and resists flowing as runoff due to inhalation, exhalation, and gravity.

Catheter 115 may taper at or near the tip. If tapered, catheter 115 may be guided to a portion of the lungs where the circumference of a bronchus or bronchial is less than the circumference of a portion of catheter 115, causing catheter 115 to become wedged within the bronchus or bronchial. Once wedged within the bronchus or bronchial, catheter 115 isolates a volume of the lungs.

Further shown in FIG. 3, auxiliary shaft 305 extends distally beyond medium outlet 303 and includes auxiliary opening 307 and sensor 309. Auxiliary shaft 305 provides space within catheter 115 allowing for auxiliary functions. For example, auxiliary shaft 305 may receive another medium or a gas from medium control device 111, 113 to be dispensed through auxiliary opening 307 to a treatment target either simultaneous with, before, or after the dispensing of the primary medium from medium outlet 303. As noted above, auxiliary shaft 305 may also provide suction to remove the medium from the lungs. Suction by auxiliary shaft 305 may occur after dispensing of the medium or during dispensing of the medium, creating a medium path from medium outlet 305 to auxiliary opening 307 and continually moving the medium past target tissue located therebetween. Suction may also occur prior to dispensing of the medium in order to cause the lung to collapse to allow for the dispensed medium to more easily make contact with infected and damaged tissue, or to remove localized mucus and other contaminants in the area to be treated in order to ensure the tissue itself is exposed to the treatment being delivered (e.g., antibiotics).

Auxiliary shaft 305 may also contain one or more wires (not shown) connecting sensor 309 to automatic medium control device 111 or workstation 80. Sensor 309 generates signals according to measurements in the target treatment region, and automatic medium control device 111 or workstation 80 receives the signals. Automatic medium control device 111 or workstation 80 process the signals and adjust medium flow parameters accordingly and/or display, on display 806, the measured data. Measurement data from sensor 309 may include pressure, temperature, acidity, acoustic readings, location within an electromagnetic field, flow rate of the medium or air in or out of auxiliary opening 307, lung airflow, if the lung segment is still functioning, imaging data (e.g., localized ultrasound), and other useful data that may inform navigation, medium dispensing, or lung status. Such functions may be performed with any known sensors or monitor suitable for a given purpose.

Referring now to FIG. 4, a diagram view of exemplary distal end 117 of catheter 115 is shown within walls W of a segment of a luminal network. Distal end 117 of catheter 115 includes medium channel 401 and medium outlet 403. As in FIG. 3, medium travels through medium channel 401 exits medium outlets 403 and enters a segment of a luminal network. When the procedure is complete, the medium is withdrawn from the segment of a luminal network and returns to medium control device 111, 113.

With further reference to FIG. 4, distal end 117 of catheter 115 further includes balloon air channel 405 within catheter 115, catheter balloons 407 coupled to catheter 115, using, for an example an adhesive bond, and balloon air passage 409 connecting balloon air channels 405 and catheter balloons 407. Automatic medium control device 111, a syringe similar to manual medium control device 113, or another air pressure device generates pressurized air that is forced through balloon air channel 415. The pressurized air exits air channel 405 balloon air passage 409 and enters catheter balloons 407, causing catheter balloons 407 to expand to contact walls W. When fully inflated, catheter balloons 407 create a pressure seal between catheter balloons 407 and walls W such that medium cannot flow beyond the points of contact between catheter balloons 407 and walls W. As the medium exits medium outlets 403, the medium fills a volume between walls W and catheter balloons 407. Limiting medium flow to this volume ensures the medium will contact walls W to cleanse the treatment target and kill bacteria.

Distal end 117 of catheter 115 further includes pressure sensor 411 coupled to or manufactured within catheters 115. Pressure sensor 411 may utilize any suitable method to determine air or medium pressure, including, for example, measuring variances in piezoresistive features, capacitance, electromagnetic inductance, and potentiometric due to displacement and strain cause by the pressure. Pressure sensor 411 may communicate via wires (not shown) running the length of catheter 115 or wirelessly with workstation 80 or automatic medium control device 111. Data from pressure sensor 411 may be displayed at workstation 80 or used in determining dispensing time and pressure by workstation 80 or automatic medium control device 111. As the medium fills the volume between walls W and catheter balloons 407, pressure within the volume increases. If pressure sensor 411 senses a pressure that exceeds a predetermined pressure, Application 81 may halt the application of the medium.

Medium pressure is monitored by pressure sensor 411 to ensure a pressure level is not exceeded that would cause harm to the lungs or force liquid beyond catheter balloons 407. If the pressure exceeds a predetermined pressure, dispensing of the medium may be halted, dispensing pressure may be reduced, or a volume of the medium may be removed either manually or automatically. Additionally, it may be preferable to cause a segment of the lungs to collapse before dispensing the medium. To cause segmental collapse, air may be removed from the lungs through medium outlets 403 using a pump or syringe. Automatic medium control device 111 and manual medium control devise 113 may also be used to perform the air removal. As the segment of the lungs collapses, pressure sensor 411 measures the pressure and can indicate when the lung has fully collapsed and is ready for the medium dispensing. Using a similar process, mucus and other contaminants can also be removed from the area prior to treatment.

FIG. 4 further shows lung bypass channel 413 extending distally beyond catheter balloon 407 and including bypass opening 415 located at the distal most end of bypass channel 413. Bypass channel 413 allows air segment to pass distally beyond the lung segment between catheter balloons 407, either by natural respiration or by ventilation. In doing so, the lung branch distal to the treatment target receives oxygen and may therefore continue to expand and contract while performing normal or near normal respiration. No air entry point is shown in FIG. 4. It should be appreciated that an opening may be may be located anywhere along the length of the catheter to allow air to enter bypass channel 413. Bypass channel 415 may also run the length of catheter 115 and thus air would enter bypass channel 415 at the proximal end of the catheter.

FIG. 4 shows two catheter balloons 407. However, it should be appreciated that catheter 115 could include only one catheter balloon 407. A single balloon would isolate an entire bronchus or bronchiole rather than merely a segment. When the medium is dispensed, the medium flows to fill the volume of the bronchus of bronchiole. For such a purpose, catheter 115 may be any suitable balloon catheter known in the art capable of being advanced within a working channel of a bronchoscope 50 or EWC 96.

Referring now to FIG. 5, a diagram view of another exemplary distal end 117 of catheter 115 is shown within walls W of a portion of a luminal network. Exemplary distal end 117 of catheter 115 of FIG. 5 possesses similar features as and operates similarly to exemplary distal end 117 of catheter 115 shown in FIG. 4. FIG. 5 further includes endobronchial valve 501. Endobronchial valves 501 typically allow air to pass out of the lung bronchus or bronchiole but do not allow air to pass back into the lung segment. As shown in FIG. 5 the endobronchial valve 501 has a reversed orientation from its typical deployment. In such a configuration the catheter 115 can easily pass through the endobronchial valve 510 and access the lung volume distal of the endobronchial valve 501. In this configuration the catheter 115 can be used to perform all of the functions described herein above with the balloon catheter embodiments including collapsing the lung volume, extracting mucus and contaminants, and injecting treatments or washing solutions. Further to create a segment for treatment, two such valves may be employed. This variation may further employ a catheter 115 with a separate oxygen or air passage allowing the portions of the lungs distal the distal most endobronchial valve 510 to be ventilated. A pressure sensor 503 monitors the application of the medium into the lungs. One advantageous aspect of the use of endobronchial valves is that a number of segments can be created in different portions of the lungs, each can receive its treatment and where desired the treatment may be left in place while the catheter 115 is repositioned and navigated to a second and continue in a segment by segment process of applying treatment, leaving the treatment at the segment for proper absorption, etc., and then subsequently removed, with the endobronchial valves being the last component to be removed.

Figure 6:
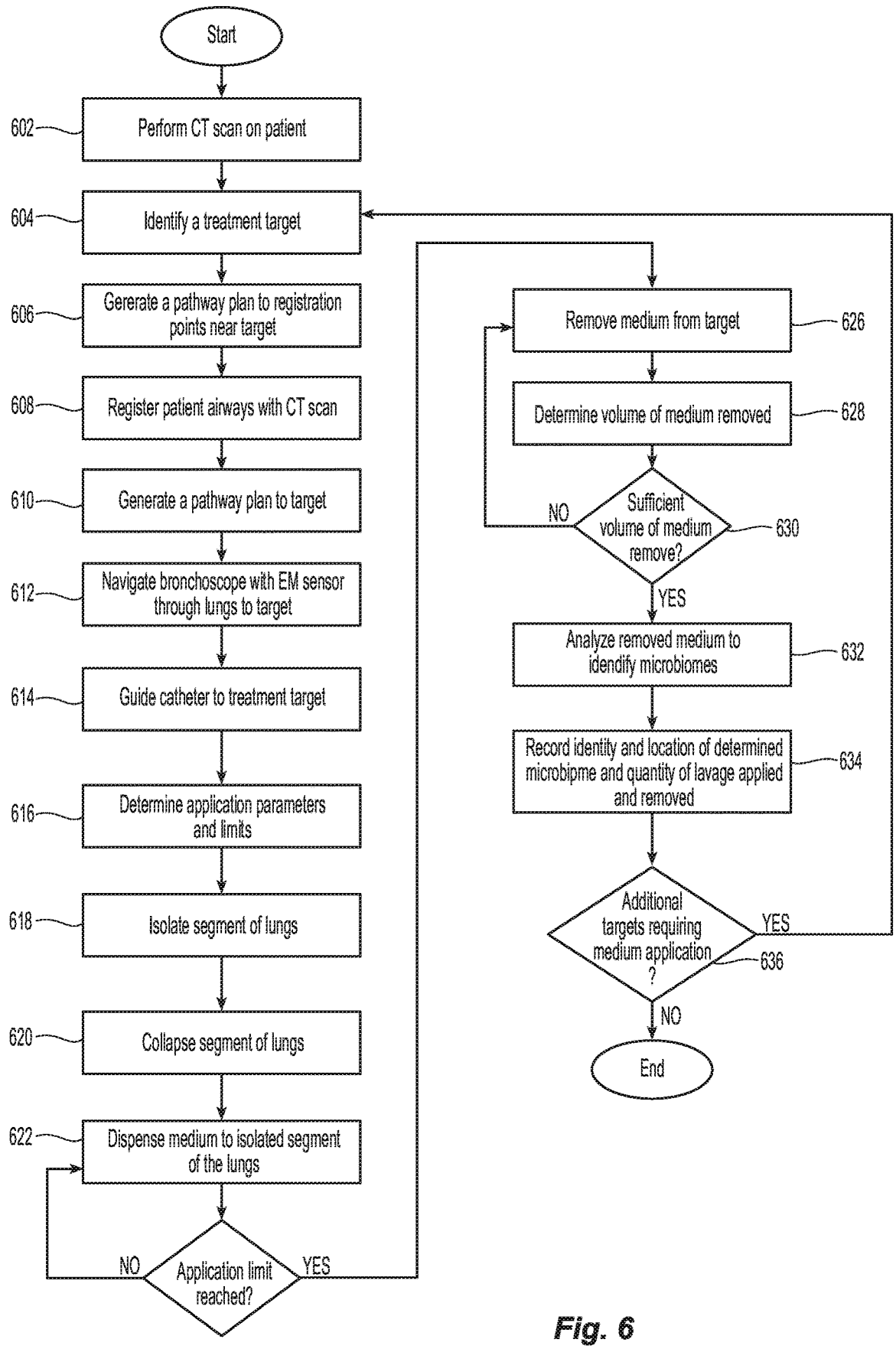
FIG. 6 is a flow chart of a method of instilling or cleansing a treatment target with medium.

FIG. 6 is a flow chart of a method of instilling or rinsing a treatment target with the medium. Beginning at step S602, an area of interest, for instance the chest and lungs, of a patient is imaged using imaging methods such as, for example, a CT scan. At step S604, a target is identified in the images generated in step S602. Once a target is established, at step S606, a path through the branches of the airways to the registration points near the target are generated in the CT image data. Once the pathway plan has been developed and is accepted by the clinician, the pathway plan can be utilized in a navigation procedure using the EMN system 10. The pathway plan is loaded into an application on workstation 80 and displayed. Then, at step S608, application 81 performs the registration of the CT scan with the patient's airways, as described above, and in particular as described in co-pending U.S. patent application Ser. No. 14/790,581, entitled REAL TIME AUTOMATIC REGISTRATION FEEDBACK, filed on Jul. 2, 2015, by Brown et al., the entire contents of which is incorporated herein by reference. During registration, the location of EM sensor 94 within the patient's airways is tracked, and a plurality of points denoting the location of EM sensor 94 within the EM field generated by EM generator 76 is generated. When sufficient points have been collected, the application 81 compares the locations of these points to the 3D model and seeks to fit all the points within the lumens of the 3D model. When a fit is established, signifying that the majority if not all of the points have been fit within the area defined by the 3D model of the airway, the patient and the 3D model are registered to one another. As a result, detected movement of the EM sensor 94 within the patient can be accurately depicted on the display of the workstation 80 as a sensor 94 traversing the 3D model or a 2D image from which the 3D model was generated.

Once a treatment target is established, at step S610, a path through the branches of the airways to the target is generated in the CT image data by Application 81. After the pathway plan has been developed and is accepted by the clinician, the pathway plan can be utilized in a navigation procedure using the EMN system 10. Application 81 begins navigation process, at step S612 by displaying guidance for navigating EM sensor to the treatment target while tracking the location of EM sensor 94. In the alternative, by viewing a live video feed from a camera located proximate EM sensor 94 (e.g., in a bronchoscope) a target may be detected visually by a clinician. Once bronchoscope 50 and/or EWC 96 are navigated to a target treatment site, at step S614, catheter 115 is guided through bronchoscope 50 or EWC 96 to the treatment target.

At step S616, preparation for dispensing of the medium begins. Medium dispensing parameters, such as, e.g. a medium quantity, volume, dispensing time, and flow rate, are determined. Additionally, dispensing limits, such as, e.g. maximum and minimum flow rate and pressure, may also be determined. Medium dispensing parameters may also come preprogrammed with factory settings.

At step S618, a segment of the lungs containing the treatment target is isolated from the rest of the lungs to limit the interference of respiration by the medium being dispensed. Isolation includes establishing a barrier using one or more catheter balloons 407 or endobronchial valves 501 or guiding distal end 117 of catheter 155 through the lung until it becomes lodged within a passageway. In some instances, an entire bronchus or bronchiole may be isolated using a single barrier. A section of a bronchus or bronchiole may be isolated using two or more isolation devices. To establish a medium barrier using a catheter balloon 407, pressurized air is injected or pumped into an air channel 405 within catheter 155, or alternatively within bronchoscope 50 or EWC 96, either manually or mechanically. The air travels through air channel 405 until it reaches catheter balloons 407, inflating catheter balloons 407 and causing catheter balloons 407 to contact and dispense pressure to the lung walls.

At step S620, air is removed from the lung segment which can cause it to collapse. By removing the air from the lung segment, the medium can more easily be dispensed without building undue pressure and ensures that the medium makes contact with the walls of the lungs to provide a thorough cleaning. Air may be pumped or drawn out using a syringe or vacuum pump, or alternatively, endobronchial valve 501 may be used. This step may also have the effect of removing mucus and other contaminants in the lungs. Once the air has been removed from the lung segment, the medium dispensing begins at step S622. Plunger 119 of manual medium control device 113 is depressed pushing the medium through catheter 115 to the collapsed segment. Work station may also control automatic medium control device 111 to produce pressure to push the medium through catheter 115 to the potentially collapsed segment.

The medium applied to the treatment target may include various healing and cleansing substances. Antibacterial, antifungal, and antiviral solutions may be utilized to kill any microbes within the lungs. Additionally, the medium may be used to introduce an immunotherapeutic treatment to treat infections or cancer. Immunotherapeutic solutions, including active, passive, and hybrid immunotherapies, may be deposited in a region near a treatment target. The immunotherapeutic solution arouses the patient's immune system local to the treatment target and increases the patient's ability to naturally fight of bacteria colonies, other infections, or cancer at the treatment target.

The medium applied to the treatment target may come in many forms and may be applied for a variety of reasons. A fluid, including liquids and gases, may be used, particularly if the lung has collapsed and the medium is necessary to reflate the lung segment. The fluid fills the lung segment ensuring that the lung segment is treated completely. Furthermore, a fluid provides a good medium for cleansing and for applying various treatments in a single solution. A fluid's cleansing ability comes from its atomic mobility which permits turbulent motion of the medium to ensure several forceful interactions with the area and any microbes to be cleansed. A fluid, also, provides a good medium to create a solution that may include antibacterial, antifungal, antiviral, and immunotherapy elements.

The medium may also include an epoxy or sealant. Diseases requiring cleansing and other treatments may create a pulmonary laceration, tear, or puncture or render the lung tissue porous. Where a tear or porous surfaces in the lungs develops, isolating the portion of the lungs containing the tear or porosity prevents air from escaping the lungs and allows for a sealing treatment using a sealant or epoxy. When introduced into the isolating lung segment, the sealant or epoxy can bind to openings in the lung walls to seal them. In the case of an epoxy, two paths within the catheter are required such that the two portions of the epoxy can remain separate until the portions reach the lung segments. In addition to sealing merely the tears and other unwanted openings in the lung segment, a lung segment may be in such disrepair that a physician may opt to seal the entirety of the lung segment. Such circumstance may occur due to an aggressive microbial colony creating several tears or it may occur due to tissue removal, such as that to remove a tumor within the lungs. In either circumstance, sealing the entire lung segment allows the lungs to function normally.

At step S624, it is determined if either a dispensing limit, a previously determined value intended to prevent against or indicate failure of the system or harm to the patient, has been achieved or exceeded, or if no input medium or no time on a timer set and maintained at workstation 80 remains. If the input medium or dispensing timer expires, the process may proceed to step S626. If there is more input medium and more time remain on the dispensing timer, the process returns to step S622 and the medium continues to be pumped through catheter 115 to the collapsed segment, unless a dispensing limit is achieved or exceeded. Predetermined values intended to prevent against or indicate failure may include, for example, pressure, applied medium volume, and medium flow rate.

As medium is dispensed to the collapsed segment containing the treatment target, sensors within automatic medium control device 111, along the length of EWC 96, bronchoscope 50, or catheter 115, and at distal end of catheter 115 monitor various aspects of the medium dispensing process. Sensors include medium flow sensor 116, which determines the flow of medium through catheter 115, pressure sensor 411, 503, which determines pressure at or near the medium dispensing, and sensor 309 may make various measurements as described above. If the measured pressure, medium flow, or any other measurement measured by the various sensors equals or exceeds a predetermined value, either set at step S516 or prior as, for example, a factory setting, then the medium dispensing stops and proceeds to step S626. The process only returns to step S622 if input medium remains, the timer has not run out, and no dispensing limit has been reached.

Throughout the medium application process, application 81 may monitor the location of EM sensor 94 and display the location on display 706. By monitoring during medium application, application 81 or a physician monitoring display 706 may ensure that distal end 117 of catheter 155 remains within the target area. During medium application, increased pressure as well as medium motion may cause distal end 117 of catheter 155 to move. If distal end 117 of catheter 155 moves more than a minimal amount, there is a risk that the treatment area may cease to be isolated or that the medium may flow to an unintended portion of the lungs causing breathing difficulty. Application 81 may automatically cause automatic medium control device 111 to cease medium application if application 81 determines that distal end 117 of catheter 155 has moved more than a threshold amount according to the measured location of EM sensor 94.

Once the medium has stopped dispensing, the medium remains within the isolated segment, which, at this point in the process, is filled, at least in part, with medium and is therefore no longer fully collapsed. The medium may remain in the isolated segment for a period of time to allow the medium to kill or dislodge bacteria or other microbes from the treatment target. Once the medium has remained on the lungs for a suitable amount of time, as determined by a timing function performed by application 81 on workstation 80, step S626 may begin. At step S626, vacuum pressure is generated by medium dispensing device 110. The medium may be withdrawn using manual medium control device 113. A clinician ensures that catheter 115 and manual medium control device 113 have an air tight connection before retracting plunger 119 and suctioning the medium. The medium may be withdrawn using automatic medium control device 111. Workstation 80 controls automatic medium control device 111 to generate a vacuum and suction the medium.

At step S628, a volume of the removed medium is measured or determined. The volume may be measured simply by a clinician observing the medium in a graduated container, including a medical syringe or pipet used to withdraw the medium. Within automatic medium control device 111, the medium may be weighed to establish a close approximation of the volume or the volume may be measured using visual sensors in a known volume container. The volume of medium removed may also be determined using medium flow sensor 116. The measured volume of removed medium may then be transmitted or manually input to workstation 80. Workstation 80 may also receive non-volume measurements and convert the measurement data into a volume measurement.

If the removed medium is less than the medium dispensed into the isolated lung segment, a volume of medium likely remains in the isolated lung segment. If the medium remaining in the lung segment is significant, it may cause respiratory complication when catheter 115 is removed and the medium flows freely in the lung. Also, remaining medium may contain bacteria that, rather than being washing away or killed, are merely repositioned within the lungs. Therefore, as step S630, if the volume of medium removed from the lungs not substantially equal to the volume of medium dispensed into the lung or if the volume of medium removed from the lungs does not exceed a predetermined volume or threshold percentage of the applied medium volume, the process returns to step S626 to remove remaining medium until the medium volumes are substantially equal or exceed the volume or percentage thresholds. If the medium volumes are substantially equal or exceed the volume or percentage thresholds, the process proceeds to step S632. During the application of medium, some of the medium may be absorbed by the lung. The amount of absorbed medium is often proportional to the volume or the lung wall surface area being treated. Therefore, rather than ceasing medium removal when volume of removed medium is substantially equal to the volume of applied medium, medium removal may end when a lesser volume of medium, dependent on the lung volume or lung wall surface area, has been removed. The rate of medium absorption may further be calculated based on a number of factors, including, but not limited to, internal pressure, internal temperature, type of medium, lung damage, and patient age.

At step S632, the removed medium undergoes analysis to identify any particulates that washed out of the lung segment with the removed medium. Removed particulates include, for example, microbiomes, cellular breakdown products, volatile compounds such as nitrous oxide, chemicals indicating drug levels, and metabolites such as potassium. A centrifuge may be used to extract microbiomes from the removed medium. By modulating the centrifuge's rotational speed, bacteria, viruses, and fungi separate out for sample.

After chemical processing of the bacteria, viruses, and fungi, the microbiomes undergo DNA testing to determine their genetic code and match the results with known genetics structures.

Solid cellular breakdown products, volatile compounds, drug may similarly be separated from the removed medium with a centrifuge. Alternatively or in addition, the removed medium may be further be analyzed to determine the composition of the removed mixture using mass spectrometry, gas chromatography, absorption photometry, atomic absorption and inductively coupled plasma mass spectrometry, ion chromatography, and nuclear magnetic resonance. Substances determined through analysis of the mixture may indicate a level of success of drug therapy, the extent and type of lung damage, and recent presence of additional microbiomes that may no longer be present.

At step S634, data regarding the microbiomes and other particulates within this medium is saved in a network. The microbiomes data is linked with further information including the location within the lungs where the microbiomes came from, the type and quantity of medium applied to and removed from the lungs. This data may be saved to a patient data file for future reference. The data allows a clinician to determine whether the applied medium at the applied volume likely succeeded in killing or removing the microbiomes at the treatment target. The data further informs future procedures. A clinician may applying the same lavage medium to further target locations of the patient's lungs if the lavage medium first applied was successful or a different lavage medium according to what the medium that is best suited to eliminating the microbiomes know to be in the lungs. Additionally, data modeling the lungs may be saved in the same file aiding and informing any subsequent procedure. The microbiomes data may also be saved on a server and compiled with data from other patients. The server can then analyze microbiomes types and locations within the lungs to establish general data to better diagnose patients based on statistical analysis.

Finally, at step S636, clinician or program 81 determines whether there are further treatment targets to cleanse. If there are further treatment targets, after deflating catheter balloons 407 if necessary, catheter 155, EWC 96, and/or bronchoscope 50 withdraw from the first treatment target, and the process returns to step S604 and repeats until there are no longer treatment targets requiring cleansing. If there are no more targets, the process ends.

As described above, rather than treating each treatment target serially, the use of endobronchial valves 501 allows of the creating of a number of segments within the lung that can be created, treated, and left in place of a desired period of time. As each segment is created and treated, the clinician can move to the next until all have been created and treated and only following treatment of all the segments begin removing the treatment mediums and the endobronchial valves from the patient.

Figure 7:
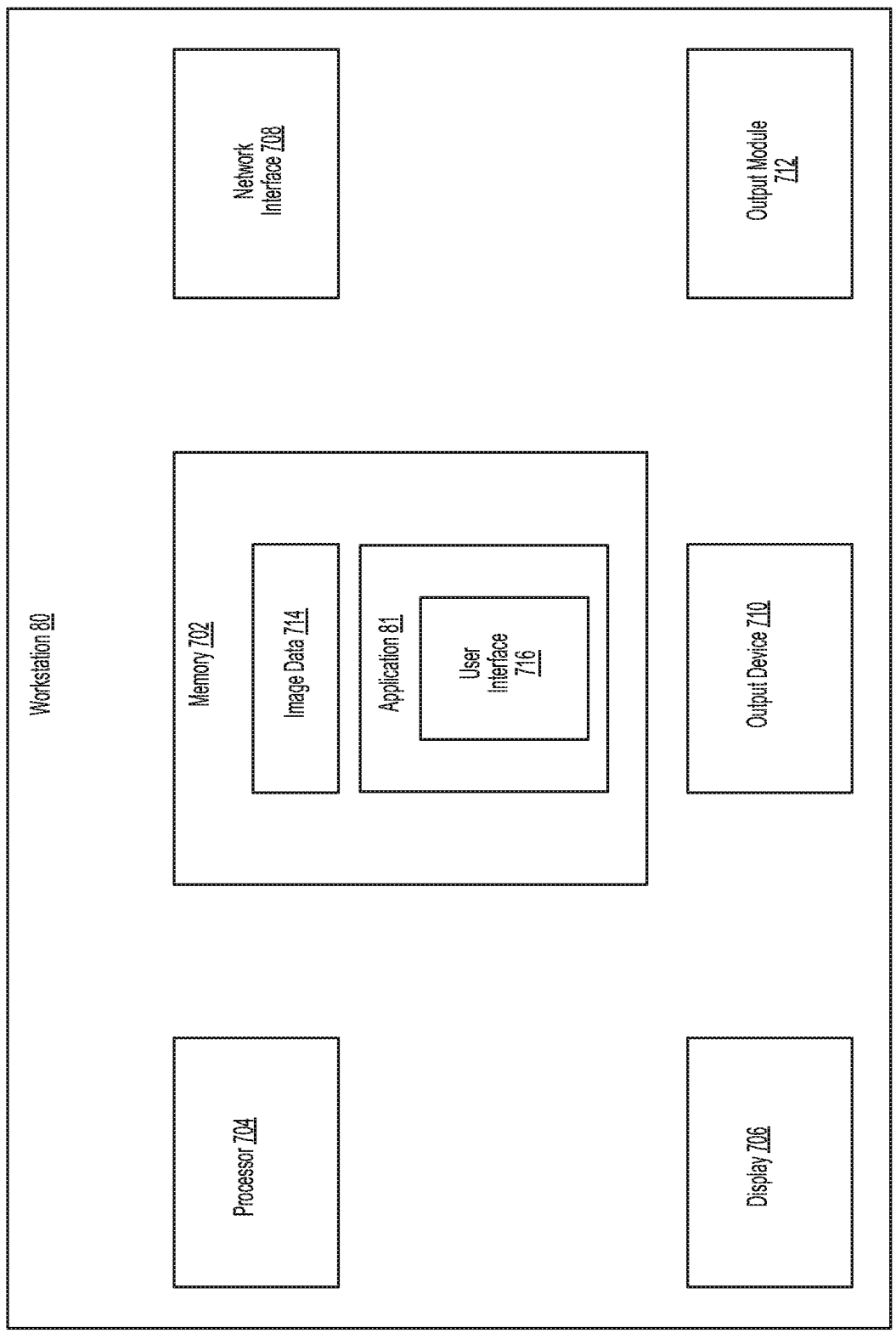
FIG. 7 is a schematic block diagram of a workstation configured for use with the system of FIG. 1.

Turning now to FIG. 7, there is shown a system diagram of workstation 80. Workstation 80 may include memory 702, processor 704, display 706, network interface 708, input device 710, and/or output module 712. Memory 702 includes any non-transitory computer-readable storage media for storing data and/or software that is executable by processor 704 and which controls the operation of workstation 80. In an embodiment, memory 702 may include one or more solid-state storage devices such as flash memory chips. Alternatively or in addition to the one or more solid-state storage devices, memory 702 may include one or more mass storage devices connected to the processor 704 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 704. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 702 may store application 81 and/or CT data 214. Application 81 may, when executed by processor 704, cause display 706 to present user interface 716. Network interface 708 may be configured to connect to a network such as a local area network (LAN) consisting of a wired network and/or a wireless network, a wide area network (WAN), a wireless mobile network, a Bluetooth network, and/or the internet. Input device 710 may be any device by means of which a clinician may interact with workstation 80, such as, for example, a mouse, keyboard, foot pedal, touch screen, and/or voice interface. Output module 712 may include any connectivity port or bus, such as, for example, parallel ports, serial ports, universal serial busses (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

Detailed embodiments of such devices, systems incorporating such devices, and methods using the same are described above. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure. While the example embodiments described above are directed to the bronchoscopy of a patient's airways, those skilled in the art will realize that the same or similar devices, systems, and methods may also be used in other lumen networks, such as, for example, the vascular, lymphatic, and/or gastrointestinal networks.

What is claimed:
1. A system for instilling medium into an isolated portion of a luminal network comprising:
  an extended working channel navigable to a treatment target within a patient; and
  a catheter, extendible through the extended working channel and configured to transport medium to the treatment target, the catheter including:

a distal end and a proximal end;
an isolation mechanism configured to contact walls of the luminal network in order to prevent the medium and air from passing, thereby isolating a portion of the luminal network;
an inlet at the proximal end configured to receive the medium;
an outlet proximal the distal end configured to dispense the medium to the treatment target proximal the isolation mechanism; and
an air channel extending distally beyond the isolation mechanism, allowing air to bypass the isolated portion of the luminal network.

2. The system of claim 1, wherein the isolation mechanism includes one or more inflatable balloons near the distal end of the catheter configured to inflate and contact the walls of the luminal network in order to create a barrier.

3. The system of claim 1, wherein the isolation mechanism includes an endobronchial valve.

4. The system of claim 1, further comprising:
a location sensor coupled to the extended working channel;
an electromagnetic field generator configured to detect the location of the location sensor as it is navigated within the luminal network;
a display capable of displaying an image of the location sensor; and
a computing device including a processor and a memory storing instructions which, when executed by the processor, cause the computing device to:
generate a model of the luminal network based on images of the luminal network;
identify the treatment target within the model of the luminal network; and
track the location of the location sensor while the location sensor is navigated within the luminal network.

5. The system of claim 1, further comprising:
a medium meter configured to measure a volume of the medium as it passes the inlet.

6. The system of claim 1, wherein the medium is one or more of an antibacterial, an antifungal, an antiviral, an immunotherapeutic solution, a fluid, an aerosol, a powder, an epoxy, and a sealant.

7. The system of claim 1, further comprising a pressure sensor configured to determine if a portion of the luminal network has collapsed or if an internal pressure of the portion of the luminal network has exceeded a pressure threshold.

8. The system of claim 1, further comprising:
a bag coupled to the catheter and configured to hold the medium; and
a valve configured to be toggled to between an open and a closed position to allow flow of the medium to and from the bag.

9. The system of claim 1, further comprising:
at least one of a pump or a syringe configured to push the medium through the inlet and out the outlet to the treatment target and to withdraw the medium from the treatment target.

10. The system of claim 1, further comprising a shaft extending distally beyond the distal end of the catheter, the shaft including an aperture configured to provide suction during or after dispensing of the medium from the outlet, such that the outlet and the aperture form a defined flow path for the medium to flow from the outlet to the aperture.

11. A catheter for instilling medium into a portion of a luminal network, the catheter comprising:
a distal end and a proximal end;
an isolation mechanism configured to contact walls of the luminal network to isolate a portion of the luminal network;
an inlet at the proximal end configured to receive the medium;
an outlet near the distal end configured to dispense the medium to a treatment target proximal the isolation mechanism; and
an air channel extending distally beyond the isolation mechanism and configured to allow air to bypass the isolated portion of the luminal network.

12. The catheter of claim 11, wherein the isolation mechanism includes one or more inflatable balloons near the distal end of the catheter configured to inflate and contact the walls of the luminal network to create a barrier.

13. The catheter of claim 11, wherein the isolation mechanism includes an endobronchial valve.

14. The catheter of claim 11, further comprising:
a location sensor coupled to the catheter;
an electromagnetic field generator configured to detect the location of the location sensor as it is navigated within the luminal network;
a display capable of displaying an image of the location sensor; and
a computing device including a processor and a memory storing instructions which, when executed by the processor, cause the computing device to:
generate a model of the luminal network based on images of the luminal network;
identify the treatment target within the model of the luminal network; and
track the location of the location sensor while the location sensor is navigated within the luminal network.

15. The catheter of claim 11, further comprising a medium meter configured to measure a volume of the medium as it passes the inlet.

16. The catheter of claim 11, wherein the medium is one or more of an antibacterial, an antifungal, an antiviral, an immunotherapeutic solution, a fluid, an aerosol, a powder, an epoxy, and a sealant.

17. The catheter of claim 11, further comprising a pressure sensor configured to determine if a portion of the luminal network has collapsed or if an internal pressure of the portion of the luminal network has exceeded a pressure threshold.

18. The catheter of claim 11, further comprising:
a bag coupled to the catheter and configured to hold the medium; and
a valve configured to be toggled between an open position and a closed position to allow the medium to flow to and from the bag.

19. The catheter of claim 11, further comprising:
at least one of a syringe or a pump configured to push the medium through the inlet and out the outlet to the treatment target and to withdraw the medium from the treatment target.

20. The catheter of claim 11, further comprising a shaft extending distally beyond the distal end of the catheter, the shaft including an aperture configured to provide suction during or after dispensing of the medium from the outlet, such that the outlet and the aperture form a defined flow path for the medium to flow from the outlet to the aperture.

* * * * *